United States Patent [19]

Barthomeuf et al.

[11] Patent Number: 4,751,346

[45] Date of Patent: * Jun. 14, 1988

[54] PROCESS FOR SEPARATING ETHYLBENZENE FROM XYLENES BY SELECTIVE ADSORPTION ON A GALLIUM BETA ZEOLITE (ATD-35)

[75] Inventors: Denise M. Barthomeuf, Lyon, France; Lawrence G. Daniel, Crosby, Tex.

[73] Assignee: Exxon Research & Engineering Co., Florham Park, N.J.

[*] Notice: The portion of the term of this patent subsequent to Apr. 22, 2003 has been disclaimed.

[21] Appl. No.: 855,093

[22] Filed: Apr. 22, 1986

Related U.S. Application Data

[63] Continuation-in-part of Ser. No. 666,196, Oct. 29, 1984.

[51] Int. Cl.$^4$ .......................... C10G 25/03; C07C 7/13
[52] U.S. Cl. ................... 585/828; 208/310 Z
[58] Field of Search ................ 208/310 Z; 585/828; 502/62, 354, 400

[56] References Cited

U.S. PATENT DOCUMENTS

| | | | |
|---|---|---|---|
| 3,308,069 | 3/1967 | Wadlinger et al. | 502/62 |
| 3,636,121 | 1/1972 | Stine et al. | 260/674 SA |
| 3,686,342 | 8/1972 | Neuzil | 260/674 SA |
| 3,686,343 | 10/1972 | Bearden et al. | 208/310 Z |
| 3,793,305 | 2/1974 | Bond | 208/310 Z |
| 3,835,043 | 9/1974 | Geissler et al. | 210/31 C |
| 3,855,333 | 12/1974 | Neuzil | 260/674 SA |
| 3,864,416 | 2/1975 | Campbell et al. | 260/674 A |
| 3,878,127 | 4/1975 | Rosback | 252/455 Z |
| 3,894,108 | 7/1975 | Geissler | 260/674 SA |
| 3,894,109 | 7/1975 | Rosback | 260/674 SA |
| 3,903,187 | 9/1975 | Geissler | 260/674 SA |
| 3,943,182 | 3/1976 | Neuzil et al. | 260/674 SA |
| 4,265,788 | 5/1981 | Ebitani et al. | 252/455 Z |
| 4,376,226 | 3/1983 | Rosenfeld et al. | 565/828 |
| 4,554,398 | 11/1985 | Barthomef et al. | 585/828 |
| 4,584,424 | 4/1986 | Barthomeuf | 208/310 Z |

FOREIGN PATENT DOCUMENTS 0037129 11/1979 Japan .
1330956 9/1973 United Kingdom .

Primary Examiner—Helen M. S. Sneed
Assistant Examiner—Glenn Caldarola
Attorney, Agent, or Firm—D. E. Furman

[57] ABSTRACT

The invention relates to a process for selectively adsorbing ethylbenzene from a stream containing one or more isomeric xylenes. The ethylbenzene is adsorbed on a gallium Beta zeolite. A desorbent comprising para-dialkylbenzene gives the zeolite good ethylbenzene selectivity over the xylenes.

6 Claims, No Drawings

PROCESS FOR SEPARATING ETHYLBENZENE FROM XYLENES BY SELECTIVE ADSORPTION ON A GALLIUM BETA ZEOLITE (ATD-35)

CROSS-REFERENCE TO RELATED APPLICATION

This application is a continuation-in-part of co-pending application Ser. No. 666,196 filed Oct. 29, 1984, allowed.

FIELD OF THE INVENTION

This invention relates to a process for selectively separating ethylbenzene from a feedstream containing one or more isomeric xylenes by using a Beta zeolite and one or more of a group of organic desorbents. The preferred desorbents are monosubstituted benzenes where the substituent contains a heteroatom, monoalkylbenzenes, and paradialkylbenzenes.

BACKGROUND OF THE INVENTION

Some crystalline aluminosilicates, or zeolites, are useful as adsorbents in separating a particular hydrocarbon compound from mixtures of hydrocarbons containing the compound. In particular, zeolites are widely used for selective separation of paraxylenes from mixtures containing other $C_8$ aromatic compounds such as metaxylene, orthoxylene, or ethylbenzene. For example, U.S. Pat. Nos. 3,636,121; 3,686,342; 3,686,343; 3,835,043; 3,855,333; 3,878,127; 3,894,108; 3,903,187 and 4,265,788 are all directed towards a method of removing paraxylene from mixtures or of selectively separating paraxylene and ethylbenzene from mixtures containing other components, using various types of zeolites as adsorbents. Paraxylene is a commercially important aromatic hydrocarbon isomer since its use in the manufacture of terephthalic acid is a critical step in the subsequent production of various fibers such as Dacron.

This invention, however, relates to a process for separating ethylbenzene from a feed mixture containing ethylbenzene and at least one other xylene isomer and is therefore unrelated to paraxylene separation processes. Additionally, in the process disclosed herein, ethylbenzene is selectively adsorbed in relation to the less selectively adsorbed xylene isomers.

While a separation of paraxylene from other xylene isomers is desirable in certain circumstances, it has become increasingly desirable to recover ethylbenzene from streams containing both ethylbenzene and xylene isomers. Ethylbenzene has great commercial importance since it is a building block in the production of styrene. Further, the cost of producing ethylbenzene by the reaction of benzene with ethylene has steadily increased. These costs have prompted research efforts in the recovery of ethylbenzene from various $C_8$ aromatic feedstreams which already contain ethylbenzene. Such feedstreams may be $C_8$ aromatic extracts resulting from various solvent extraction processes, from pyrolysis gasoline, or from reformed naphtha.

It is known that zeolite Beta has been used to adsorb mixtures of paraxylene and ethylbenzene selectively from mixtures comprising ethylbenzene, orthoxylene, metaxylene and paraxylene using toluene as a desorbent. See U.S. Pat. No. 3,793,385 to Bond et al., issued Feb. 19, 1974. Bond et al. additionally suggests a large number of cations including Li, K, Cs, Mg, Ca, Sr, Ba, La and Ce may be included in the zeolite. Cs and K are especially preferred.

However, the invention disclosed herein is based on the discovery that certain desorbents modify the behavior of zeolite Beta so that it adsorbs ethylbenzene in substantial preference to paraxylene and the other isomeric xylenes. Generically, these desorbents belong either to the family of monosubstituted benzenes wherein the substituent contains a heteroatom selected from the group consisting of O, S, P, and the halogens (particularly halobenzenes; for instance, iodobenzene) and alkylbenzenes with a linear side chain, or to the family of paradialkylbenzenes (particularly, p-ethyltoluene, p-diethylbenzene and p-methyl n-propylbenzene).

Other zeolite systems are known which selectively adsorb ethylbenzene from mixed $C_8$ aromatic streams in the presence of diethylbenzene as desorbent. One such process is disclosed in U.S. Pat. No. 3,943,182 to Neuzil et al., issued Mar. 9, 1976. However, the zeolites disclosed therein are either Type X or Type Y. The adsorptive activity of a particular type of zeolite is not easily predictable, if it is predictable at all. Indeed, the direction in which zeolite selectivity is affected by a particular desorbent is even less predictable.

SUMMARY OF THE INVENTION

The invention disclosed herein is directed to a process for selectively adsorbing ethylbenzene from feedstreams containing both ethylbenzene and mixtures of xylenes. The process utilizes Beta zeolites and certain desorbents. The desorbents may be generically described as monoalkylbenzenes, paradialkylbenzenes and mono-substituted benzenes having a heteroatom selected from the group consisting of O, S, P and the halogens in the substitutent group. This combination of desorbent and zeolite provides simultaneously acceptable values for the selectivities of the ethylbenzene as compared to paraxylene, metaxylene, or orthoxylene. These desorbents are unique in that they increase each ethylbenzene selectivity factor with respect to the xylene isomers.

Ethylbenzene can be separated and recovered from a feedstream mixture containing at least one and preferably all isomeric xylenes by the process made up of (a) contacting the hydrocarbon mixture with a Beta zeolite, so that the contacting takes place under conditions to affect a selective adsorption of ethylbenzene by the zeolite, (b) passing through the zeolite, during or after the contacting step, a desorbent which produces a selectivity factor ($\alpha$ EB/xylene) for each xylene which is greater than about 2 under the same conditions, and which has a desorbent strength factor ($\alpha$ EB/desorbent) in the range of 0.1 to 10, and (c) recovering from the zeolite a stream enhanced in the concentration of ethylbenzene relative to the isomeric xylenes.

The selectivity factor, which represents the selectivity of the adsorbent for ethylbenzene over a particular xylene, is defined by the expression:

$$\alpha \text{ EB/xylene isomer} = \frac{\text{amount of ethylbenzene in zeolite}}{\text{amount of ethylbenzene in non-adsorbed phase}} \times$$

$$\alpha = \frac{\text{amount of xylene isomer in non-adsorbed phase}}{\text{amount of xylene isomer in zeolite}}$$

The desorbent strength factor, which represents the selectivity of the adsorbent for ethylbenzene over the desorbent, is defined by the expression:

$$\alpha \text{ EB/desorbent} = \frac{\text{amount of ethylbenzene in zeolite}}{\text{amount of desorbent in non-adsorbed phase}} \times$$

$$\frac{\text{amount of desorbent in non-adsorbed phase}}{\text{amount of desorbent zeolite}}$$

DESCRIPTION OF THE PREFERRED EMBODIMENT

The feedstream mixtures which are applicable to the present invention comprise at least ethylbenzene and one xylene isomer. Preferably the feedstream contains ethylbenzene and all of the xylene isomers. In addition, the feedstream mixture may contain up to about 20%, preferably less than about 10 volume percent, of non-aromatic components such as paraffins, cycloaliphatic or olefinic compounds. Such components will tend to be adsorbed by the zeolite in smaller amounts than the aromatic components. Whatever else may be present in the mixture, however, the process embodies the technique of separating ethylbenzene from various xylenes.

Feedstream mixtures containing $C_8$ aromatics such as ethylbenzene and xylene isomers are generally obtained via such processes as reforming, pyrolysis and isomerization. The paraxylene isomer is often extracted from this mixture by the processes of crystallization, extraction, or selective adsorption, thus leaving a feedstream relatively rich in ethylbenzene and metaxylene and substantially depleted in paraxylene. The process steps described herein as part of the invention may be used after such a paraxylene separation process or preferably may be used before such a process. The latter method improves the efficiency of the overall process since the paraxylene recovered should then have a higher purity with no ethylbenzene impurity.

In the process described herein, the ethylbenzene is separated from the xylene isomers in the feedstream mixture by contacting the mixture with the zeolite adsorbent defined below in such a manner that the ethylbenzene is more selectively adsorbed than the xylene isomers. Concurrently with this contacting step, or subsequent thereto (if the operation is a batch operation), desorbents are passed through zeolites so as to desorb the enriched ethylbenzene containing phase formed adsorbed on the zeolite.

The zeolite contacting step may be conducted in a batch or continuous mode of operation. For example, the adsorbent may be placed in a fixed bed which is intimately contacted with a feedstream mixture containing ethylbenzene and xylene along with a desorbent or it may be placed in a fluidized bed which is contacted with a mixture and a desorbent in a continuous operation. The fluidized bed may be used with or without magnetic stabilization and with or without real or simulated co- or countercurrent flows. Where the adsorbent is employed in a static bed, the process may be semicontinuous, e.g., or operated as a pulsed chromatographic process. The adsorbent may be placed in a set of two or more static beds such that the feedstream mixture is contacted with one bed while the desorbent is passed through one of the others. In some instances, it may be desirable to remove a least-adsorbed component from the voids in a bed by flushing with a very weakly adsorbed material, e.g., a paraffin, before recovery of ethylbenzene by addition of the desorbent. Moving or simulated moving beds represent a preferred mode of operation because of the greater efficiency in the resulting separation.

Temperatures for contacting and desorption steps of the process herein may vary broadly depending, inter alia, on the desorbent used, but generally will range from about room temperature to about 300° C. Similarly operating pressures will vary considerably but generally will range from about atmospheric to about 30 atmospheres (3 megapascals) pressure.

The desorbent employed in the present invention may be defined as a compound which is characterized by its minimum ability to enhance the selectivity of Beta zeolites in separating ethylbenzene from xylene isomers and by maintaining those selectivities above about 2.0. The selectivity is expressed herein as a selectivity factor, designated $\alpha$ EB/xylene isomer, which is defined above. The value of the selectivity factors should be as high as possible. Too low a factor will result in poor separation between two components.

Another parameter which characterizes the desorbent herein is the strength of the desorbent, which is expressed by a desorbent strength factor, designated $\alpha$ EB/desorbent as defined above. This factor represents the ratio of the adsorption strength of the zeolite for the ethylbenzene to the adsorption strength of the zeolite for the desorbent. If the desorbent is too strongly adsorbed relative to the ethylbenzene, i.e., so that the desorbent strength factor is less than 0.1, then both ethylbenzene and the xylenes will be eluted at a similar time. On the other hand, a desorbent having a desorbent strength factor of greater than about 10 will not compete favorably with the ethylbenzene, necessitating large volumes of desorbent to recover all the ethylbenzene. The ethylbenzene thus collected would be contained in a large amount of desorbent so that an expensive and energy-consuming distillation procedure would be required to recover the ethylbenzene. The desorbent strength factor ratio is preferably in the region of about 1 to about 2, but for the purposes herein is generally in the range from about 0.1 to about 10.

The desorbents applicable to the disclosed process may be generically described as monoalkylbenzenes, paradialkylbenzenes and monosubstituted benzenes having a heteroatom substituted in the ring.

The alkyl substituent of the monoalkylbenzene preferably contains two to twelve carbon atoms. Especially preferred are those compounds belonging to the group consisting of n-butylbenzene, n-pentylbenzene, n-heptylbenzene, n-nonylbenzene and dodecylbenzene. Most preferred of this group is n-nonylbenzene. In addition, mixtures of two or more desorbents which have the requisite characteristics may also be employed as desorbents desired. The desorbent may be diluted with a liquid inert material such as a paraffin or a cycloparaffin.

Another class of desorbents producing excellent ethylbenzene selectivity on Beta zeolites is made up of the paradialkylbenzenes. The alkyl chains may be of any convenient length. Preferably the alkyl moieties are fairly short chains, i.e., less than five carbon atoms. Especially preferred compounds include p-ethyltoluene, p-diethylbenzene and paramethyl-n-propylbenzene. Again, these compounds may be used as mixtures either with other paradialkylbenzenes, monosubstituted benzenes or inert diluents such as paraffins, cycloparaffins or olefins.

Monosubstituted benzenes having a heteroatom in the substituent group are also quite useful in this invention. The heteroatom should be selected from the group consisting of S, O, P, and the halogens. Especially preferred are the monohalobenzenes, particularly iodobenzene.

The zeolite Beta has a poorly understood structure. However, U.S. Pat. No. 3,308,069 (which is incorporated by reference) describes a method of preparing the zeolite. Bond et al., discussed above, additionally describes methods for producing the zeolite and for exchanging the zeolites with various alkali and alkaline earth metal cations. An integral portion of this invention involves use of Beta zeolites containing at least one cation selected from the group consisting of alkali and alkaline earth metals, and mixtures thereof. It has been found that the selectivity of zeolite Beta increases with the size of the substituent cations. Consequently, rubidium substituted Beta provides better selectivity than does potassium and cesium substituted Beta is even better still. Zeolite Beta substituted with potassium gives better selectivity than do those substituted with sodium.

By zeolite Beta is meant the zeolite having as its structure that disclosed in U.S. Pat. No. 3,793,385. The zeolite within this definition may have any atomic Si/Al and the framework may include other atoms such as Ga or B partially or fully substituted for aluminum, or Ge or P partially or fully substituted for silicon. The positive charges of the zeolitic framework must be substantially neutralized by one or more types of cations.

Zeolite Beta containing gallium has been found effective in the separation of ethylbenzene from the xylene isomers. When cesium-substituted gallium Beta is the adsorbent and p-diethylbenzene is the desorbent, the observed order of selectivity with respect to $C_8$ aromatic isomers is as follows: ethylbenzene > paraxylene > orthoxylene > metaxylene.

After the feedstream mixture and desorbent have been contacted with the zeolite, the respective eluted product streams containing the various components are directed to separate recovery vessels. The stream which is enhanced in ethylbenzene content due to the separation achieved by the adsorption and desorption operations may be further processed to recover the ethylbenzene by, e.g., distillation, or other suitable recovery techniques.

The following examples further illustrate the efficacy of the present invention and in these examples all parts or percentages are given by weight and all temperatures are in degrees Centigrade unless otherwise indicated.

EXAMPLE 1

Beta zeolite was produced in the presence of excess tetraethylammonium hydroxide using the procedure outlined in U.S. Pat. No. 3,308,069. The starting zeolite had an atomic Si/Al ratio of 13.3 and contained (weight %) $SiO_2=94.71\%$, $Al_2O_3=6.0\%$, $Na=0.37\%$, $K=500$ ppm and $N=1.6\%$. About 90% of the cations saturating the framework negative charges were tetraethylammonium and there were excess ions trapped in the cages. The zeolite was then calcined at about 500° C. for more than 15 hours to remove the organic cations. Other methods of removing the template organic cations would, of course, be acceptable. Separate portions of the cationated zeolite were then exchanged with chloride solutions of the various alkaline cations, dried, exchanged at room temperature, dried, exchanged at room temperature, washed and dried again. The exchanged zeolites were then dehydrated in a 550° C. oven flushed with dry nitrogen for at least 15 hours.

About three hundred milligram samples of the dried zeolite were transferred each to a series of 2-ml vials sealed with a septum cap. To each bottle was added, by syringe, the respective feed in an amount representing the capacity of the zeolite. The vials were agitated at room temperature for 2 to 24 hours under ambient conditions to reach adsorption equilibrium. The vapor phase above the zeolite was analyzed by gas chromatograph. Due to the selectivity of adsorption, the vapor pressures reflect the composition of the liquid phase in equilibrium with the zeolite. From the gas chromatograph peaks, the α EB/xylene isomer and α EB/desorbent factors were calculated.

TABLE 1

Changes in Selectivities with Desorbents for Various Beta Zeolites
Feed Equimolar $C_8$ Aromatics:Desorbent

| | EB | | | | $C_8$:Desorbent |
|---|---|---|---|---|---|
| | PX | MX | OX | Des | (by Mole) |
| H—Beta | | | | | |
| No desorbent | 1.2 | 2.4 | 2.0 | — | — |
| Na—Beta | | | | | |
| No desorbent | 1.4 | 3.1 | 2.6 | — | — |
| p-diethylbenzene | 1.5 | 2.3 | 1.9 | 1.7 | 1:2 |
| K—Beta | | | | | |
| No desorbent | 1.6 | 5.2 | 4.3 | — | — |
| n-butylbenzene | 1.4 | 4.3 | 3.0 | 1.4 | 1:2 |
| Benzene | 1.6 | 2.8 | 5.2 | 0.9 | 1:3.2 |
| Toluene | 1.8 | 4.1 | 3.2 | 1.3 | 1:2 |
| p-diethylbenzene | 2.5 | 4.7 | 3.3 | 3.6 | 1:2 |
| Rb—Beta | | | | | |
| No desorbent | 2.0 | 7.4 | 5.2 | — | — |
| Benzene | 1.6 | 2.7 | 1.8 | 1.1 | 1:3.2 |
| Toluene | 1.7 | 4.9 | 3.6 | 2.2 | 1:2 |
| n-butylbenzene | 2.1 | 4.7 | 3.1 | 1.4 | 1:2 |
| n-pentylbenzene | 2.4 | 4.3 | 2.9 | 2.3 | 1:2 |
| Iodobenzene | 2.6 | 10.1 | 5.9 | 8.7 | 1:2 |
| p-diethylbenzene | 4.6 | 9.3 | 5.1 | 5.6 | 1:2 |

Table 1 shows that when zeolite Beta is substituted by the alkali metal cations, benzene and toluene as desorbents provide generally unacceptable selectivities for zeolite Beta. Substitution of the larger cations into the zeolite allows for enhanced selectivities with a number of desorbents. Paradiethylbenzene was clearly best in all cases.

EXAMPLE 2

An additional amount of zeolite Beta was produced as in Example 1. After calcining to remove the included organic ammonium template cation, one portion was exchanged with cesium chloride twice (with drying) to produce Cs-Beta I. Other methods of removing any such organic template would, of course, also be acceptable. A second portion was treated with the process described for Cs-Beta I, dried at 120° C., dried at 550°

C. under flushing nitrogen, cooled and re-exchanged twice at room temperature. The second portion is referred to as Cs-Beta II. A third and separate portion of the starting batch was treated in the manner described for CS-Beta II and is referred to as Cs-Beta III.

Various desorbents were added to the zeolites in the method specified in Example 1. The resulting selectivities are shown in Table 2.

TABLE 2

Changes in Selectivities ($\alpha$) with Desorbents for Cs—Beta Zeolites
Feed Equimolar $C_8$ Aromatics:Desorbent

|  | EB | | | | $C_8$:Desorbent |
| --- | --- | --- | --- | --- | --- |
|  | PX | MX | OX | Des | (by Mole) |
| Cs—Beta I | | | | | |
| No desorbent | 2.1 | 7.6 | 6.1 | — | — |
| Benzene | 2.0 | 3.0 | 2.4 | 0.6 | 1:3.2 |
| Toluene | 2.2 | 4.6 | 3.7 | 1.9 | 1:2 |
| n-butylbenzene | 2.4 | 4.3 | 3.3 | 1.8 | 1:2 |
| n-pentylbenzene | 2.4 | 3.9 | 3.0 | 1.8 | 1:2 |
| Iodobenzene | 2.5 | 7.7 | 5.0 | 4.9 | 1:2 |
| Cs—Beta II | | | | | |
| Prehnitene | 1.2 | 7.8 | 7.3 | 40.0 | 1:2 |
| o-diethylbenzene | 1.2 | 11.0 | 13.0 | 11.0 | 1:2 |
| Isodurene | 1.2 | 16.0 | 14.0 | 50.0 | 1:2 |
| n-dodecylbenzene | 2.0 | 6.1 | 4.3 | Not deter. | 1:2 |
| n-heptylbenzene | 2.7 | 4.8 | 3.9 | Not deter. | 1:2 |
| n-pentylbenzene | 2.8 | 5.2 | 3.7 | 1.1 | 1:2 |
| n-nonylbenzene | 3.3 | 6.6 | 4.7 | Not deter. | 1:2 |
| Cs–Beta III | | | | | |
| No desorbent | 2.2 | 9.0 | 5.2 | — | — |
| o-methyl n-propylbenzene | 0.9 | 12.3 | 16.0 | 18.0 | 1:2 |
| m-diethylbenzene | 1.3 | 16.1 | 17.0 | 26.0 | 1:2 |
| Isobutylbenzene | 1.4 | 5.4 | 4.9 | 2.0 | 1:2 |
| p-methyl n-propylbenzene | 4.0 | 8.1 | 5.4 | 4.0 | 1:2 |
| p-diethylbenzene | 5.5 | 11.3 | 7.3 | 8.0 | 1:2 |

As in Example 1, monosubstituted benzenes and paradiakylbenzenes provide superior selectivities. If the differing processes for exchanging Cs into the zeolite gave different cation loading, the difference in loading appear to result in only minor difference in performances.

EXAMPLE 3

This example compares the selectivities obtained by using the best desorbents of Example 1 and 2 on zeolites which are outside the scope of this invention. Table 3 demonstrates about unique combination of zeolite and desorbent result in enhanced selectivities.

TABLE 3

Effect of p-dialkylbenzenes on Various Ethylbenzene Selective Zeolites
Feed Equimolar $C_8$ Aromatics:Desorbent (1:2 by Mole)

|  |  | EB | | | |
| --- | --- | --- | --- | --- | --- |
| Zeolite | Desorbent | PX | MX | OX | Desorbent |
| RbX | paradiethylbenzene | 3.1 | 2.4 | 1.5 | 6.0 |
| CsX | paradiethylbenzene | 1.7 | 1.8 | 1.6 | 2.2 |

TABLE 3-continued

Effect of p-dialkylbenzenes on Various Ethylbenzene Selective Zeolites
Feed Equimolar $C_8$ Aromatics:Desorbent (1:2 by Mole)

|  |  | EB | | | |
| --- | --- | --- | --- | --- | --- |
| Zeolite | Desorbent | PX | MX | OX | Desorbent |
| CsX | para methyl n-propylbenzene | 3.6 | 3.9 | 2.3 | 9.0 |
| Rb—Beta | paradiethylbenzene | 4.6 | 9.3 | 5.1 | 5.6 |
| Cs—Beta | paradiethylbenzene | 5.5 | 11.3 | 7.3 | 8.0 |
| Cs—Beta | para methyl n-propylbenzene | 4.0 | 8.1 | 5.4 | 4.0 |

EXAMPLE 4

Gallium zeolite Beta in its hydrogen form prepared from a synthesis gel having an $SiO_2/Ga_2O_3$ molar ratio of 31.25 was cation exchanged with cesium. A C8 aromatic liquid feedstream containing 1.1% ethylbenzene, 1.1% paraxylene, 1.0% orthoxylene, 1.0% metaxylene, 1.0% triisopropyl benzene (an internal standard for the gas chromatograph), 84.7% n-heptane and 10.1% paradiethylbenzene desorbents all by weight, was added at ambient temperature (about 25° C.) to the adsorbent, with the feedstream being in excess of that which the zeolite can adsorb. After allowing this mixture to reach equilibrium, the mixture was allowed to settle and a sample was removed and analyzed by gas chromatography. The amount of C8 isomers and desorbent in the solution was measured, and the amount of isomers and desorbent was obtained by difference from the standard feedstream. The capacity and the ($\alpha$) separation factor were calculated for the C8 aromatic isomers and desorbent as listed in Table 4.

TABLE 4

| Run No. | EB/PX | EB/MX | EB/OX | EB/p-DEB |
| --- | --- | --- | --- | --- |
| 1 | 4.2 | 22.3 | 11.4 | 6.2 |
| 2 | 4.7 | 32.4 | 14.4 | 7.4 |
| 3 | 6.7 | 31.8 | 8.2 | 9.2 |

In summary, improved separation of ethylbenzene from isomeric mixtures of xylenes are possible by use of Beta zeolites in combination with certain desorbents.

What is claimed is:

1. A process for the separation of ethylbenzene from a feedstream containing ethylbenzene and at least one xylene isomer comprising the steps of:
   (a) contacting the feedstream with a gallium Beta zeolite to adsorb ethylbenzene by the zeolite;
   (b) passing a desorbent comprising paradialkylbenzene through the zeolite during or after the contacting step; and
   (c) recovering a stream enhanced in ethylbenzene concentration from the zeolites.

2. The process of claim 1 wherein the feedstream comprises orthoxylene, metaxylene and paraxylene.

3. The process of claim 2 wherein the feedstream is substantially depleted in paraxylene.

4. The process of claim 1 wherein the desorbent is paradiethylbenzene.

5. The process of claim 1 wherein the zeolite is substituted by at least one cation selected from the group consisting of alkali and alkali earth metals, and mixtures thereof.

6. The process of claim 1 wherein the zeolite is substituted by Cs cations.

* * * * *